United States Patent [19]

Burri et al.

[11] Patent Number: 5,528,026

[45] Date of Patent: Jun. 18, 1996

[54] PROCESS AND ARRANGEMENT FOR THE INSPECTION OF TRANSLUCENT ARTICLES

[75] Inventors: Karl-Georg Burri, Oberrieden; Peter Gysi, Bellikon, both of Switzerland

[73] Assignee: Elpatronic AG, Zug, Switzerland

[21] Appl. No.: 302,507

[22] Filed: Sep. 8, 1994

[30] Foreign Application Priority Data

Oct. 8, 1993 [CH] Switzerland ............... 3040/93
Jan. 5, 1994 [CH] Switzerland ............... 0020/94

[51] Int. Cl.⁶ .................................................. G01N 9/04
[52] U.S. Cl. .................. 250/223 B; 356/240; 209/526
[58] Field of Search ............... 250/223 B; 356/239, 356/240, 428; 209/524, 526

[56] References Cited

U.S. PATENT DOCUMENTS

| | | | |
|---|---|---|---|
| 3,302,786 | 2/1967 | Conrad | 209/526 |
| 4,083,637 | 4/1978 | Ellinger et al. | 356/240 |
| 4,221,961 | 9/1980 | Peyton . | |
| 4,551,627 | 11/1985 | Reich | 250/223 B |
| 4,959,537 | 9/1990 | Kimoto et al. . | |
| 5,280,170 | 1/1994 | Baldwin | 250/223 B |

FOREIGN PATENT DOCUMENTS

| | | |
|---|---|---|
| 02087396 | 7/1993 | Canada . |
| 0060918 | 9/1982 | European Pat. Off. . |
| 0555646 | 8/1993 | European Pat. Off. . |
| 3919110 | 12/1989 | Germany . |

OTHER PUBLICATIONS

Japanese Abstracts vol.4, No. 86, (P—16) (568) Jun. 20, 1980, & JP—A—55 050144 (Hajime Sangyo).

Japanese Abstract vol. 2, No. 75, (E—38) Jun. 14, 1978, & JP—A—53 040 583 (Hitachi Denshi), Apr. 13, 1978.

*Primary Examiner*—Georgia Y. Epps
*Assistant Examiner*—Jacqueline M. Steady
*Attorney, Agent, or Firm*—McCormick, Paulding & Huber

[57] ABSTRACT

According to the process of the invention, optical inspection of a translucent article, in particular optical inspection of a concave bottom of a container, in which the article is positioned between a radiation source and an image recording apparatus and an image of the article is recorded and processed, is improved by placing at least one optical correction element in the paths of rays between the radiation source and the image recording apparatus to correct ray paths causing undesired dark or black spots on the image, so that such dark or black spots are prevented or brightened in order that an adequate image for satisfactory image-analysis is produced.

14 Claims, 4 Drawing Sheets

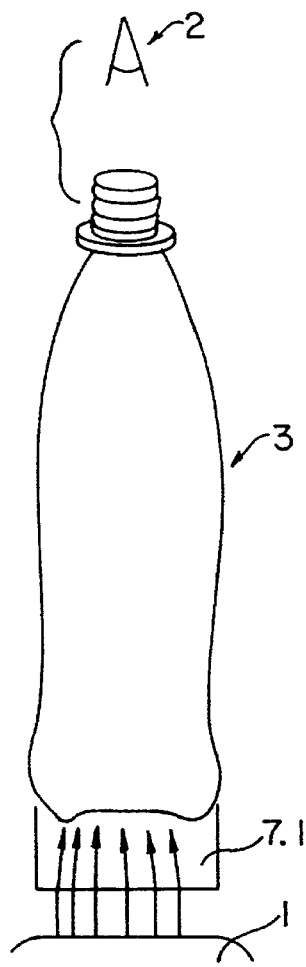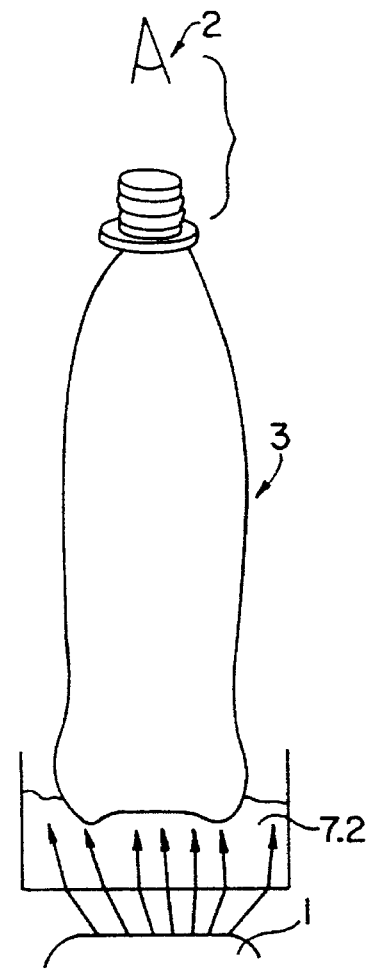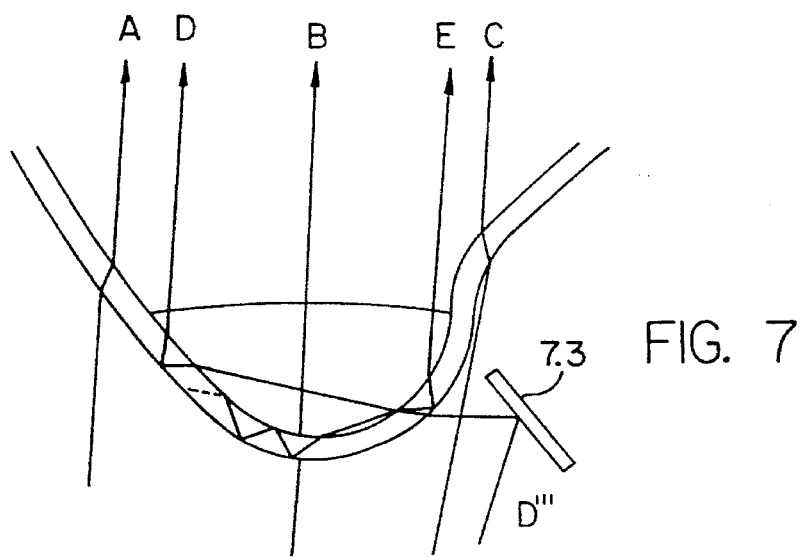

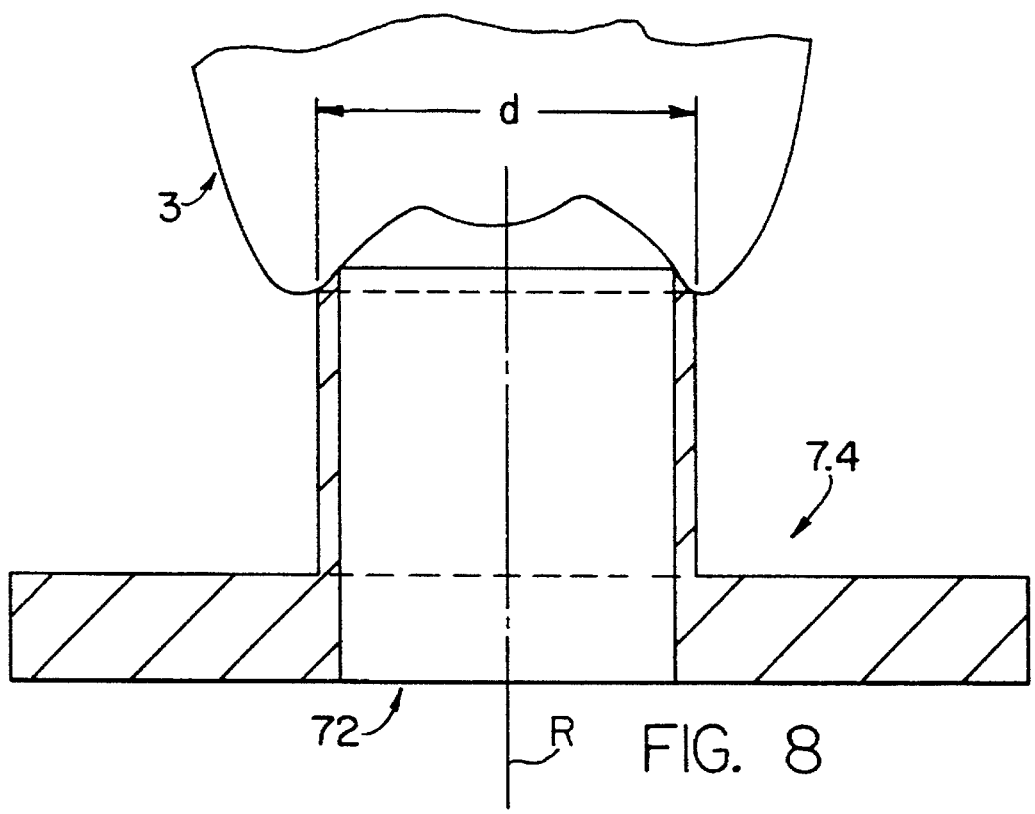
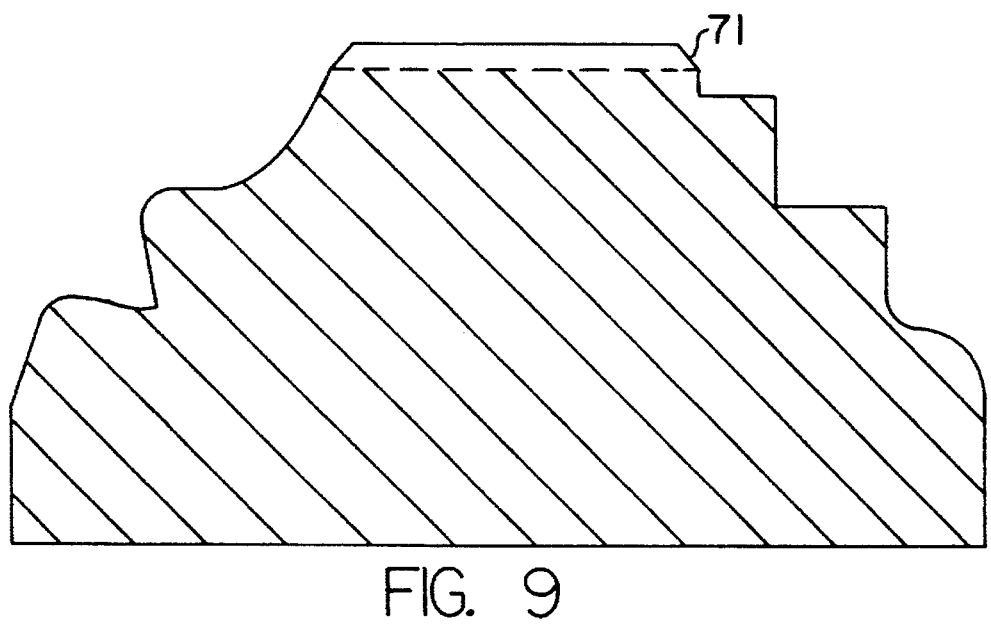

PROCESS AND ARRANGEMENT FOR THE INSPECTION OF TRANSLUCENT ARTICLES

BACKGROUND OF THE INVENTION

The invention is in the field of optical inspection by image processing, and relates to a process and an arrangement according to the introductory parts of the corresponding independent claims for optical inspection of translucent articles, in particular containers, by means of image processing.

The inspection of translucent containers by image processing is known. Such inspection may for example be used for production checks, for reading marks, or for testing returnable containers for cleanliness and absence of defects. For these purposes an image (in the widest sense of the word) is usually produced by a transmitted-light process, that is to say with an arrangement in which at least that part of the container which is to be inspected is positioned between a direct or indirect light source and an image recording apparatus, for example a camera. This image is analysed by known methods involving for example the detection and/or interpretation of dark or black spots in the image. According to the result of the image analysis, control systems may then be activated to bar the container concerned from further processing.

Soiling, marks, defects etc. are usually recognized in the images obtained as dark or black spots on an otherwise generally light background representing a clean, intact, unmarked container wall. However, it has been found that the images may contain dark and black spots due not only to marks, soiling etc. but also to the container wall itself, that is to say due to the geometry and/or surface condition of the wall or to an optical combination of undetectable liquid residues with the container wall geometry, so that, owing especially to reflection at the surfaces of the container wall, the transmitted illumination becomes non-homogeneous, that is to say, the image contains for example dark or black spots which may also shift or fluctuate, especially with arrangements operating continuously at high speed. At these spots, detection of flaws, soiling, marks etc. by means of image processing becomes impossible, or at least very difficult, as the contrast between the background and the image of an object to be detected is reduced or completely lost.

SUMMARY OF THE INVENTION

It is the object of the invention to overcome the abovementioned disadvantages of inspection of radiation-translucent and in particular light-translucent articles by means of image processing, so that inspection with a satisfactory result is made possible essentially without requiring a higher standard of radiation source, in particular light source, image recording apparatus and image processing electronics, even in cases where the article, or the region of the article, to be inspected is of such a nature that the image which it generates in a normal radiation-transmission or light-transmission process, with or without residual liquid, contains dark and/or black spots interfering with the image processing.

This object is realized by the inspection process according to the invention and the inspection arrangement according to the invention, as these are defined in the claims.

The process and arrangements according to the invention are based on correction of the path of the rays from the radiation or light source to the image recording apparatus by at least one optical correction element so that the image of the article, or region of the article, to be inspected is of a brightness which is sufficiently homogeneous to satisfy the requirements of the means used for the image processing, that is to say, the correction element produces a brightening of undesired dark or black spots on the image of the article to be inspected, mainly due to reflection at the surfaces of the container wall, so that a satisfactory inspection, even at these spots, is possible.

The optical correction element can operate in two ways. On the one hand, the element may compensate for the disturbing reflection by additionally refracting or reflecting light from the light source (or other radiation from a radiation source) to produce a ray path from the light source to the image processing apparatus whereby dark or black spots which are entirely due to the first reflection can be brightened or prevented. On the other hand, the optical correction element may modify locally the optical efficiency of the surface of the article to be inspected so that the disturbing reflection is prevented or at least reduced and so that the abovementioned dark or black spots can thereby be brightened or prevented. An optical correction element which prevents or reduces reflection at regions of a surface may consist of a material which is optically denser than air, advantageously possesses the closest possible optical properties to the material of the article to be inspected, and is in close contact with its surface so that as far as possible no optically effective air gap is present between the two materials. A correction element which refracts or reflects light rays can take the form of, for example, a suitably positioned prism, a lens, a mirror or a similar known optical element, in this case with the optical properties of the correction element adapted to the required refraction and/or reflection and not to the optical properties of the material of the article t be inspected. Alternative forms of correction element which both prevent reflection and produce refraction could also be used.

Accordingly, optical correction elements which can be used include translucent solid bodies with the closest possible optical properties to those of the container wall; translucent liquids with the same optical properties; light-reflecting surfaces (e.g. mirrors); light-refracting bodies (e.g. prisms, lenses); or combinations of the said elements. The optical correction element or elements can be placed in the corresponding paths of rays between the light source and the article to be inspected and/or between the article to be inspected and the image recording apparatus.

Diffuse, white, i.e. visible, light is preferably used for the inspection. However, the process and arrangement according to the invention can also be used in conjunction with other kinds of light (polarized, coloured or directional light), and also with electromagnetic radiation other than visible light to which the same laws of refraction and reflection apply. In other words, the light source can, generally speaking, be replaced by almost any desired radiation source provided the or each correction element is configured accordingly. The terms "translucent" and "optical" employed in this text are to be understood in a correspondingly broadened sense.

The configuration and positioning of the optical correction element or elements are to a very large extent governed by the inspection arrangement and by the article to be inspected. They may be determined by geometrical optical considerations based on the one hand on the desired homogeneous illumination of the image plane and on the other hand on the luminous radiation delivered by the light source.

It may require considerable costs to make the undesired dark zones in the generated image disappear completely by corresponding optical correction. However, it is sufficient to brighten these spots by the optical correction which has been described so as to afford sufficient contrast for the image interpretation facilities available.

Some practical examples of inspection arrangements with optical correction elements will now be described with reference to the drawings. The application which is fundamental to all these examples is the inspection of container bottoms with a "dome", i.e. concave container bottoms. However, this in no way implies that the process and arrangement according to the invention are limited in application to the inspection of such container bottoms. As has already been mentioned, the arrangement and the process can be used with the same advantages for the inspection of any translucent articles. Benefits accrue in all cases where a particular combination of inspection arrangement, geometry and/or surface condition of the article to be inspected makes inspection according to the state of the art difficult or impossible owing to dark or black spots on the image produced.

BRIEF DESCRIPTION OF THE DRAWINGS

In the drawings:

FIG. 5 shows an examples of an inspection arrangement with a translucent solid optical correction element;

FIG. 6 shows an example of an inspection arrangement with a translucent liquid optical correction element;

FIG. 7 shows a detail of an example of an inspection arrangement with a mirror as optical correction element;

FIG. 8 shows one embodiment of an optical correction element for inspecting a 0.51 soft-drink bottle made from PET; and FIG. 9 shows a further embodiment of optical correction element for inspecting a 0.51 soft-drink bottle made from PET.

BRIEF DESCRIPTION OF THE PREFERRED EMBODIMENTS

Figure 1:
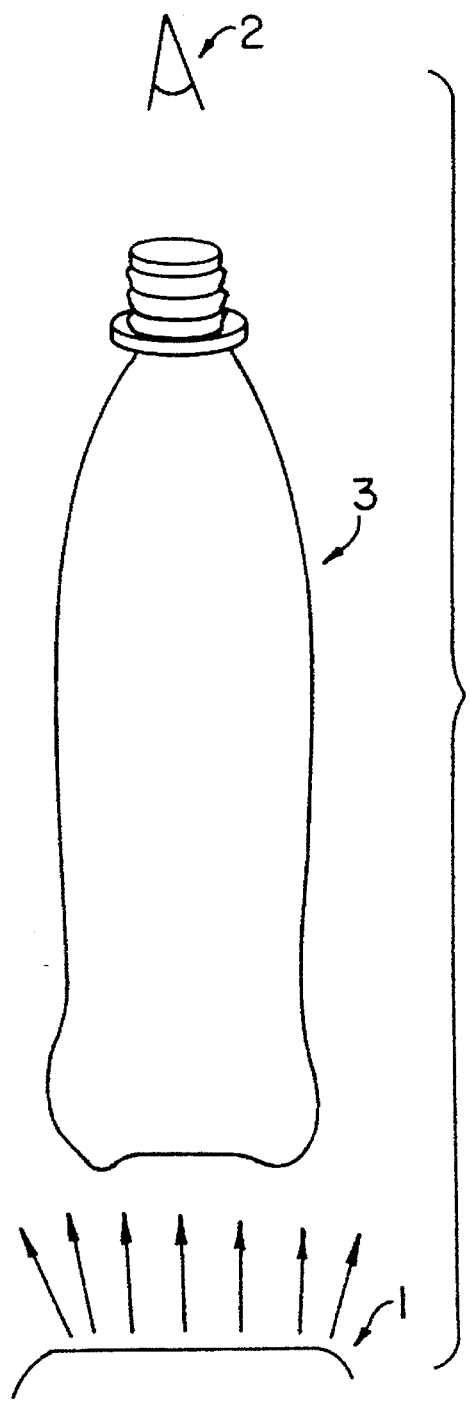
FIG. 1 shows an arrangement according to the state of the art for the inspection of a container bottom with a concave dome.

FIG. 1 shows schematically an arrangement for inspecting the bottoms of bottles, as used according to the state of the art. The arrangement comprises, for example, a source 1 of white diffuse light, an image recording apparatus 2, for example a camera, and means (not shown) for positioning the container 3 to be inspected between light source and camera. These means for positioning the container 3 are normally designed to allow containers to be positioned in very rapid succession.

Figure 2:
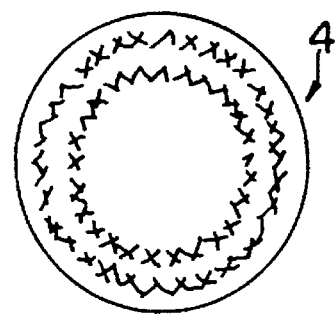
FIG. 2 shows an image of a container bottom with a dome, produced by the arrangement according to FIG. 1, with possible dark or black spots.

FIG. 2 shows an image 4 of the container bottom produced with the arrangement shown in FIG. 1. In this image, as a result of the geometry of the dome, possibly in combination with any residual liquid which is present in the container and undetected, dark or black spots may occur in the cross-hatched zones, making detection of soiling, defects, marks etc. in these zones difficult or impossible. The zones may shift if the container is not precisely centered. If the dark or black spots are due to residual liquid, they may occur in asymmetrical form in a rapid process in which the residual liquid may still be moving actually during the recording of the image (be fluctuating or dynamic).

Figure 3:
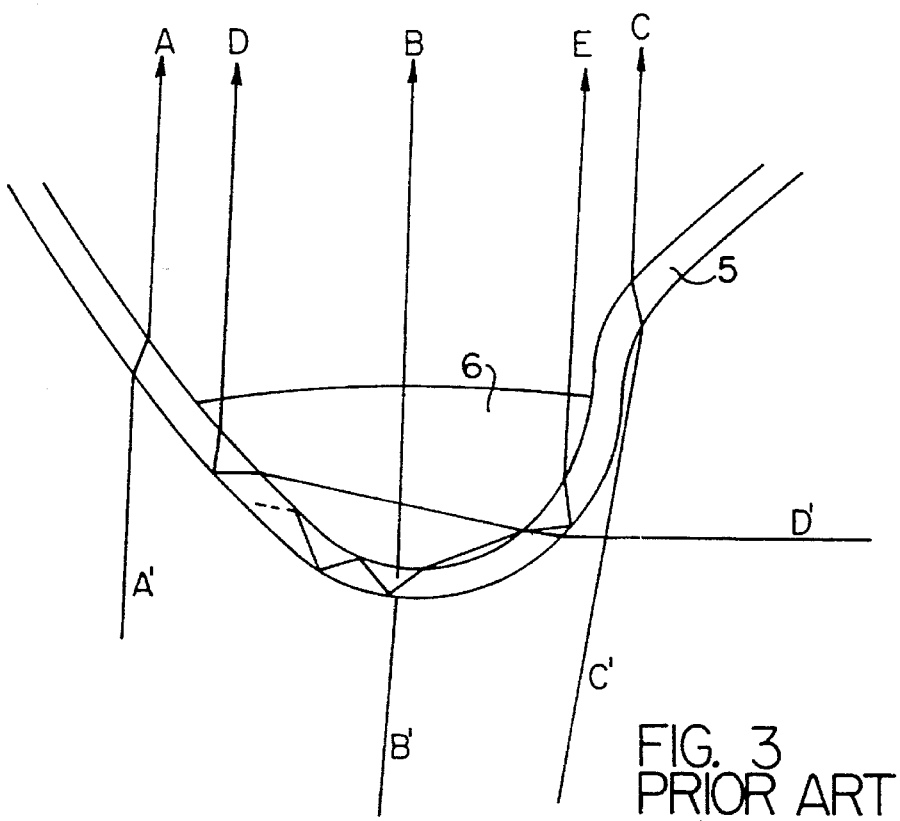
FIG. 3 shows the uncorrected paths of some rays through a container bottom with a dome.

FIG. 3 shows, on a larger scale and as a section through a lateral region of the container bottom, the path of rays through the container bottom when this is inspected in accordance with the state of the art (with the arrangement shown in FIG. 1). The figure shows a section of the container bottom 5 at the edge of the dome with a small quantity of residual liquid 6 present. The dome is not shown in its entirety, and would extend to the right as seen in the figure. The figure also shows, as examples, rays along five paths A, B, C, D, E through the illustrated region of the container bottom. For an image plane with homogeneous brightness, it is desirable to have, as illustrated, rays striking the image plane (at the top in the figure) with a density which is as uniform as possible. The figure shows that such rays can be delivered in the regions of the paths A, B, C by a diffuse light source positioned under the container bottom (A', B', C'). However, the figure also shows that rays along paths D and E cannot be supplied by the said light source, as the ray on path D would have to emanate from the direction D', and the ray on path E from somewhere within the wall 5 itself. In other words, if the light source according to the state of the art is used on its own, no rays, or few, reach the image plane along paths D and E, and the result is that dark and/or black spots may occur at these points, as illustrated in FIG. 2.

Figure 4:
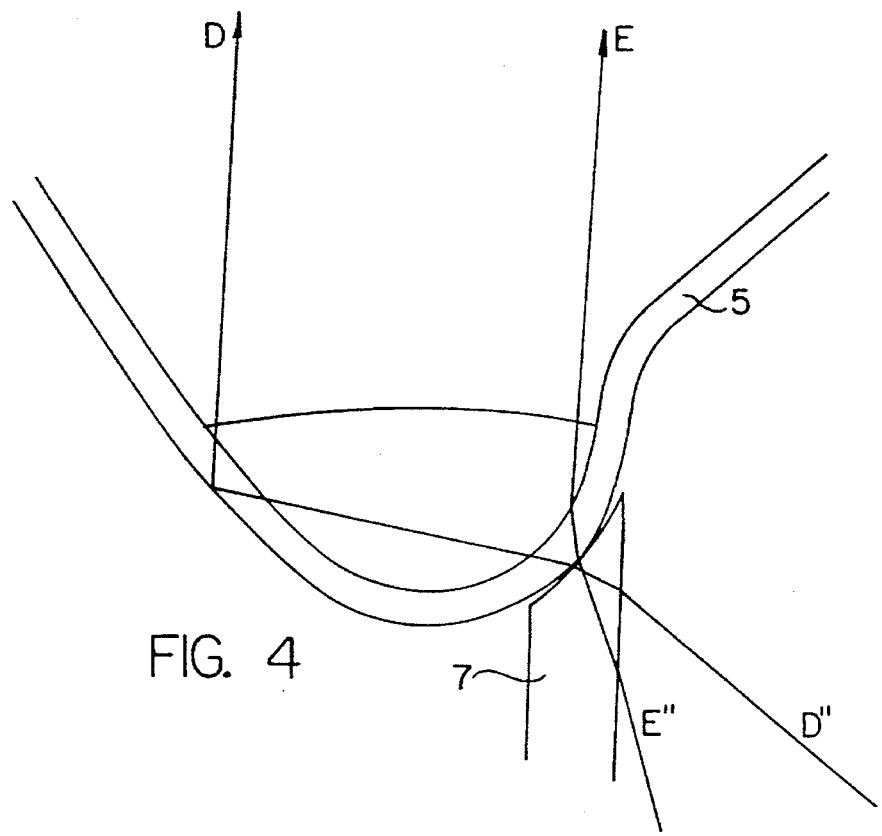
FIG. 4 shows two example of the paths of rays through a container bottom with a dome, corrected in accordance with the invention.

FIG. 4 shows the same region of a container bottom 5 as that illustrated in FIG. 3, and likewise shows the ray paths D and E from the container bottom to the image plane. An optical correction element 7 is also schematically shown in the dome edge region. This element is at least partly in close contact with the container bottom (with no air gap) and helps to reduce or prevent reflection of the ray from path E, so that this ray can be supplied from the diffuse light source (direction E"). For the ray on path D the correction element acts as a prism, so that a ray from the diffuse light source in the direction D" is refracted towards the desired ray path D, and is reflected at the container surface.

It is found that a correction element as schematically illustrated in FIG. 4 brightens the undesired dark or black spots even when these, as already stated, are not symmetrical and/or are fluctuating. That is to say, the process according to the invention which uses such a correction element satisfies the requirements of, for example, modern bottling lines operating with very high throughputs.

FIGS. 5 to 7 show in a highly schematic form examples of embodiments of the arrangement according to the invention for inspecting container bottoms with concave domes, using various optical correction elements. Again, these are arrangements for inspecting container bottoms with domes which in each case have a light source 1 for diffuse white light, an image recording apparatus 2, and means for positioning a container 3 for inspection. However—as already stated—, the process according to the invention and the arrangement according to the invention are not restricted to such an application. For other applications, the configuration and/or position of the correction element or elements must be adapted accordingly.

FIG. 5 shows an arrangement with an optical correction element 7.1 in the form of a translucent solid body with an optical density higher than air, and advantageously with an optical density approximately equal to that of the material of the container. On the side facing the light source, this body has an essentially flat surface essentially perpendicular to a line connecting the light source and camera, and a surface facing the container which corresponds to an inversion of the dome surface. The correcting body 7.1 advantageously forms part of the positioning means which hold the container to be inspected in position between camera and light source, and exerts a slight pressure against the dome. As a result the correcting body is in close contact with the dome, thus largely correcting the undesired optical phenomena at the external surface of the dome, represented in FIG. 3 by the ray paths D and E. To ensure that the correcting body is in close and optically effective contact with the container bottom, it would also be possible to force water between the correcting body and the container bottom, or to coat the correcting body with a gelatinous medium on the side facing the container bottom.

FIG. 6 shows an arrangement with a volume of liquid as the optical correction element (correcting liquid 7.2), this liquid advantageously possessing essentially the same optical properties as the material of the container. The action of the correcting liquid 7.2 is the same as the action of the correcting body described in relation to FIG. 5. Compared with the latter, however, it has the advantage that it is more effective than the correcting body in correcting undesired optical phenomena caused by local roughnesses of the container bottom, as the liquid naturally makes better contact with such roughnesses (unevenness) of the surface. It is advantageous to ensure by a suitable choice of liquid (with good wetting of the container material) and suitable insertion of the container into the liquid that no bubbles are formed, in the liquid and in particular on the surface of the container, which could themselves give rise to the undesired optical phenomena which the invention seeks to prevent, and hence to misinterpretations of the processed images. For the inspection of PET bottles, water has been found to be a suitable correcting liquid. Instead of a liquid, a gel or gelatinous substance may also be used.

Of course, to assist the image interpretation, the other side (interior) of the container bottom can also be covered with liquid. If the article to be inspected is not a hollow body, it should be wholly immersed in the liquid.

FIG. 7 shows, in a detailed representation corresponding to the illustrations in FIGS. 3 and 4, an arrangement according to the invention with a reflecting optical correction element in the form of a mirror 7.3. It can be clearly seen from the figure that the ray D which is desirable for homogeneous image-brightness, and already mentioned in relation to FIGS. 3 and 4, is reflected by means of the mirror 7.3 so that it can be supplied by the diffuse light source 1 (direction D''').

A similar action to that of a mirror is performed by the optical correction element 7 already described in relation to FIG. 4, a suitably inserted lens, or other optical element acting in the same way.

FIG. 8 shows a further detail of an advantageous optical correction element 7.4 for an arrangement for inspecting containers 3 with domed bottoms, in particular for inspecting 0.5l soft-drink bottles made from PET to check for cleanliness, to test for stress-cracking or hazing, or to read marks. The optical correction element used in this arrangement is a solid body of Perspex or Plexiglas essentially in the form of a hollow cylinder with the end face 71 facing the container adapted to fit the dome of the bottle to be inspected. The light source is positioned in the region of the opening 72 of the hollow cylinder which faces away from the container. The light source may be a direct source, i.e. for example a lamp, or an indirect source i.e. for example a mirror reflecting the light from the light source in the desired directions. The outer diameter d of the optically effective portion of the element 7.4 facing the container to be inspected is approx. 40 mm.

Such an optical correction element has been found to provide images of bottoms of the said soft-drink bottles which yield entirely satisfactory results with normal image processing facilities for bottom inspection.

The correction element illustrated in FIG. 8 is advantageously also used as the retaining element for the container 3. In this case, it should be made laterally displaceable, for example on a circular track, and rotatable about its axis of symmetry. It has been found that such a correcting/retaining element can be used not only for inspecting the whole area of the bottom of the container 3, but also—if necessary in conjunction with further image processing—for reading a code marked on the bottom. The container can then be conveyed to further processing stations where for example a code can be inscribed, or, after corresponding rotation of the container, an existing code can be altered or extended. It is also possible to perform an all-over inspection of the container walls or a leakage reading without having to transfer the container to another retaining element.

To improve the contact of the end face 71 of the correction element 7.4 with the container bottom, water can be forced between the end face 71 and the container bottom, or the end face 71 can be coated with a gelatinous compound, immediately before inspection.

FIG. 9 shows a further embodiment of a correction element for the same application as that which has been described in relation to FIG. 8. The embodiment according to FIG. 9 can be of essentially any desired shape, but at least part (71) of one end face is, again, adapted to the dome of the container bottom to be inspected. This will be sufficient to close the ray path between the radiation source and the image recording apparatus, so that it can be employed in accordance with the invention.

We claim:

1. Process for the optical inspection of a radiation-transmitting article, comprising the steps of:

generating an image of at least part of the article in a light-transmission process by means of a radiation source and an image recording apparatus, and analyzing the image by an image processing process, and preventing undesired dark spots on the image produced which occur on surfaces of the article to be inspected as a result of reflection and/or refraction, using at least one optical correction element positioned in the path of rays extending between the radiation source and the image recording apparatus.

2. Process according to claim 1 wherein the optical correction element reduces undesired reflection on surfaces of the article to be inspected, by being constituted of a radiation-transmitting and by being positioned in operative contact with at least a part of the reflecting surface.

3. Process according to claim 2, wherein the correction element is made of a material possessing an optical density essentially equal to the optical density of the material of the container.

4. Process according to claim 2, wherein the radiation or light-transmitting material is a solid, liquid, gelatinous or gel-like substance.

5. Process according to claim 1, wherein the optical correction element refracts or reflects rays from the radiation source so that, together with a reflection at the surface of the article to be inspected, the rays are directed into the image recording apparatus.

6. Process according to claim 5, wherein the optical correction element is a mirror, an optical prism or a lens.

7. Arrangement for carrying out the process of optically inspecting a radiation-transmitting article, the said arrangement comprises a radiation source;

an image recording apparatus;

means for positioning a radiation-transmitting article which is to be inspected, so that at least part of the rays generated by the radiation source is directed through the article onto the image recording apparatus during the time necessary for the recording of the image; and at least one optical correction element which is positioned in the paths of rays between the radiation source and the image recording apparatus, the optical correction element being in the form of a solid, radiation-transmitting body positioned in operative contact with at least part of a reflective surface of the article to be inspected.

8. Arrangement according to claim 7, further comprising:

means for forcing water or another liquid between the regions of the correction element and the article to be inspected.

9. Arrangement according to claim 7, wherein the optical correction element comprises a gelatinous or gel-like substance at least in the region in which the correction element is positioned in operative contact with the article to be inspected.

10. Arrangement according to claim 7 wherein the optical correction element is arranged between the radiation source and the article to be inspected.

11. Arrangement according to claim 7 wherein the optical correction element is a mirror, a prism or a lens and is positioned in ray paths which also include a reflection on regions of surfaces of the article to be inspected.

12. Arrangement according to claim 8, characterized in that the article to be inspected is a container bottom formed with a dome, that the optical correction element is essentially in the form of a cylinder or hollow cylinder, and that at least part of one end face of the optical correction element conforms at least approximately to the shape of the dome, and can be brought into contact with the exterior of the container bottom.

13. Arrangement according to claim 12, characterized in that the article to be inspected is the bottom of a plastic container and the optical correction element is made of plastic material at least partly translucent to the radiation.

14. Arrangement according to claim 13, characterized in that the container to be inspected is a plastic bottle for soft drinks.

* * * * *